United States Patent [19]

Morris et al.

[11] 4,080,664
[45] Mar. 28, 1978

[54] WELDER'S HOOD WITH AIR FILTER

[76] Inventors: Louis Morris; Lois Ann Morris, both of 1208 Radbard St., Carson, Calif. 90746

[21] Appl. No.: 647,936

[22] Filed: Jan. 9, 1976

[51] Int. Cl.² .............................................. A61F 9/06
[52] U.S. Cl. .................................................... 2/8
[58] Field of Search ................. 2/8, 9, 174; 128/141, 128/146, 146.2

[56] References Cited

U.S. PATENT DOCUMENTS

| | | | |
|---|---|---|---|
| 1,205,308 | 11/1916 | Work | 2/8 |
| 1,497,012 | 6/1924 | Goodspeed | 2/8 X |
| 2,377,122 | 5/1945 | Bakke | 2/9 X |
| 2,583,304 | 1/1952 | Pipher | 2/8 UX |
| 3,152,588 | 10/1964 | Rogowski | 2/9 X |
| 3,232,290 | 2/1966 | Nicolai | 2/8 X |
| 3,308,477 | 3/1967 | Boyd | 2/8 |

*Primary Examiner*—Werner H. Schroeder
*Assistant Examiner*—Peter Nerbun
*Attorney, Agent, or Firm*—Clarence A. O'Brien & Harvey B. Jacobson

[57] ABSTRACT

A protective welder's hood including changeable air filter structure to protect the health of a welder wearing same. The hood includes an airtight face-engaging mask together with a flutter or flapper valve to permit exhaust of expelled breathing air.

1 Claim, 5 Drawing Figures

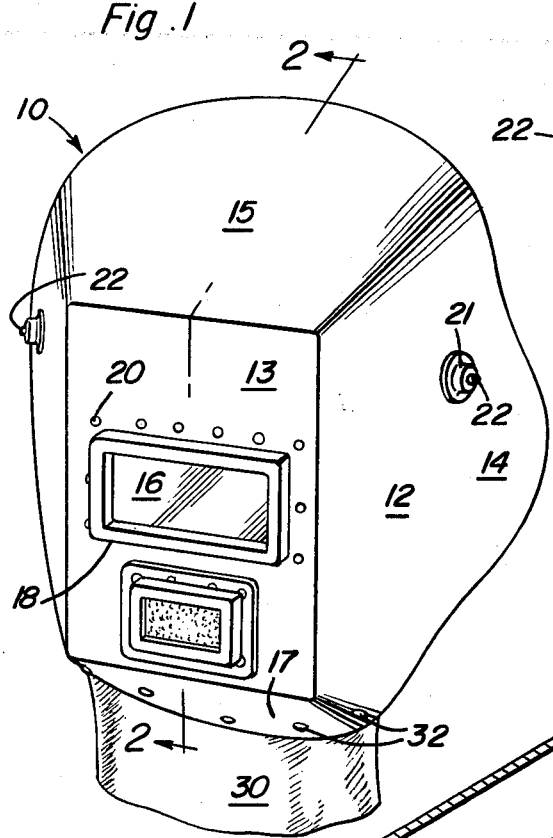
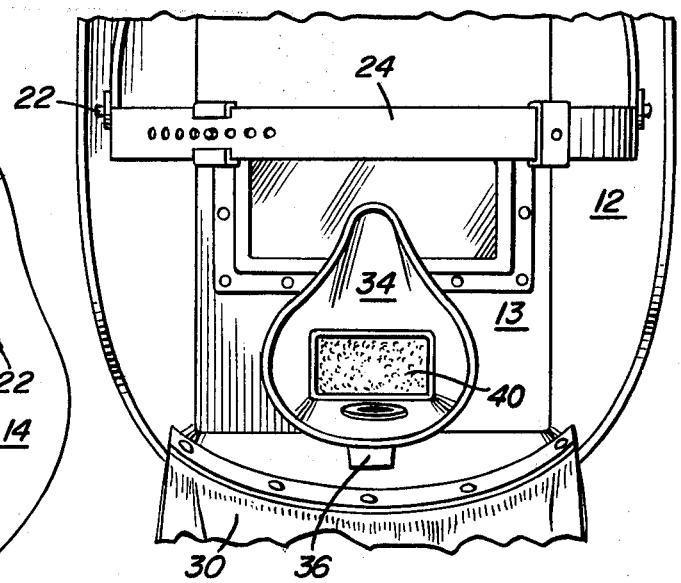
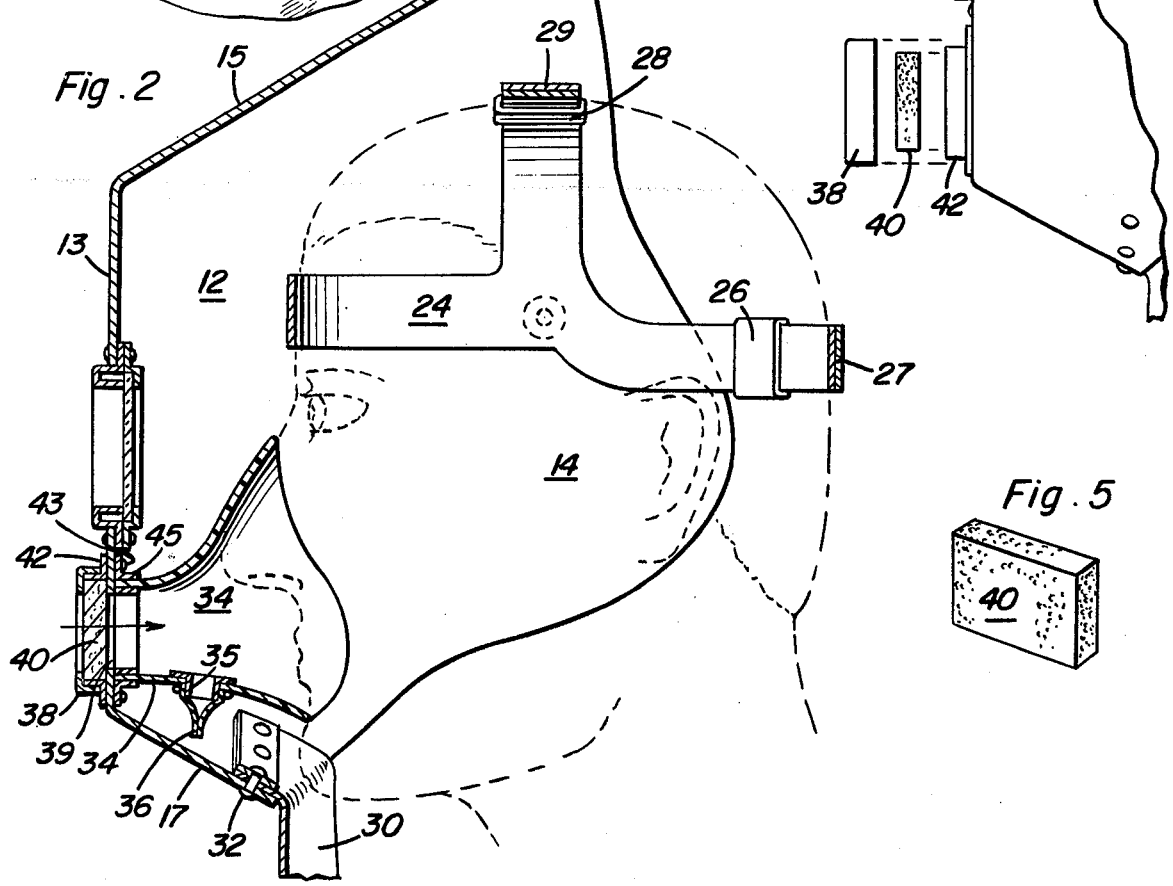

WELDER'S HOOD WITH AIR FILTER

BACKGROUND OF THE INVENTION

1. Field of the Invention

This invention relates generally to protective hood devices for use by welders which include air filtering structure to protect a welder from the poisonous and noxious fumes given off by the newer type welding rods.

2. Description of the Prior Art

A common problem with known protective hoods for welders is that they only protect the welder against damage to the eyes, and secondarily against sputtering or thrown particles of metal in the face because of the face shield only type of protective hood.

Known prior art hoods for welders do not include means for protecting a welder against poisonous or noxious fumes and gases are commonly given off by the newer type welding rods in use today.

There are known face masks or devices for protecting a wearer's lungs and breathing system, such as used by painters, workers in asbestos factories, etc. However, none of these known devices employ the other features necessary to protect a welder.

Existing prior patents which may be pertinent to this invention are as follows: U.S. Pat. Nos. 2,377,122, May 29, 1945; 2,432,311, Dec. 8, 1947; 2,583,304, Jan. 22, 1952; 2,740,400, Apr. 3, 1956; 3,438,060, Apr. 15, 1969.

SUMMARY OF THE INVENTION

An object of the present invention is to provide a protective hood for welders which is readily usable in a conventional manner together with protective means for the welder's breathing system.

Another object of this invention is to provide a hood for protecting a welder during a welding operation which includes changeable filter means and airtight face-engaging mask structure for excluding any unfiltered air from the nose and mouth of a welder wearing the device.

A further object of this invention is to provide a protective welding hood having a breathing system protection system incorporated therewith which includes an exhaust flutter valve outlet.

A still further object of this invention is to provide a protective welding hood having breathing system protecting means together with means for protecting the ears of the user.

A still further additional object of this invention is to provide a welder hood for protecting the eyes, breathing system, and also including additional structure to protect the neck of the welder.

The big advantage of the protective hood of this invention is that it does a much better job of protecting a welder using same than does the conventional type welder hood. The device of this invention protects the eyes and eyesight of a user as do conventional welder hoods, and in addition also protects the breathing system of the welder and also the ears and neck of the welder.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the protective hood of this invention.

FIG. 2 is a cross-sectional side view of this invention taken generally along line 2—2 of FIG. 1.

FIG. 3 is a view, in part, as viewed from the rear opening of the protective hood of this invention.

FIG. 4 is a view, in part, of the air filter structure shown in exploded view.

FIG. 5 is a perspective view of the air filter element.

DESCRIPTION OF THE PREFERRED EMBODIMENT

Referring to FIG. 1 of the drawing, reference numeral 10 indicates the protective welder's hood of this invention as shown in perspective. The basic hood structure comprises side panels 12 on each of the vertical sides of the front face panel 13 and a top head covering portion 15 and a bottom chin covering portion 17.

As is conventional with protective hoods for welders, a face plate 16 of appropriate radiation filtering type is provided in a mounting receptacle 18 which is permanently mounted integral with panel 13 by means such as rivets 20. The purpose of the glass or filter 16 is to remove harmful radiation and block same from the eyes of a welder. Pivot structure 21 is provided on each side of the hood for supporting pivot pins 22 which are connected to the head gear 24. As shown in FIGS. 2 and 3, said head gear is adjustable by means 26, 27 for head size and by means 28, 29 for proper positioning of the protective hood up and down on the head of a welder so that the eye filter 16 will be in proper alignment with the welder's eyes when the hood is down and in the proper position for use during welding.

An important feature of this protective hood is the extension 14 on each side 12 for the purpose of protecting a welder's ears from sputters and thrown particles of welding rod, etc. Conventional type hoods do not provide this additional protective feature.

Another additional protective feature of this welding hood is the flexible neck flap 30 which is riveted to the chin protecting portion 17 of the hood by means of fasteners such as the rivets 32 shown. The neck protector would preferably be made of asbestos or other fire-resistant material and as can be seen in FIG. 2, adds a great deal of additional protection to the lower portion of a welder's head and obviously his neck.

The air filtering structure of this invention includes a flexible face-engaging mask 34 suitably formed or molded so as to appropriately cover the nose and mouth areas of a welder with a snug fit against the face thereof so that an airtight seal is formed. The front of the face mask is appropriately fastened to flange member 45 which is in turn riveted or appropriately fastened to the front of the face shield 13 by means such as rivets 43. The outside of the protective hood has a second flange member 42 held by the same rivets 43. A rectangular opening 39 is provided in the face plate 13 which is covered by the replaceable filter element 40 and held within the flange member 42 by means of the removable cover 38. This structure is shown in expanded form in FIG. 4 of the drawings.

FIG. 5 of the drawing shows the filter element 40 which is formed of fibrous material and incorporates charcoal throughout the fibers for the purpose of removing the hazardous fumes and gases which are emitted by the newer type of welding rods.

Thus it can be seen that the filter element 40 may be easily replaced whenever the element becomes clogged and partially ineffective for its intended purpose.

Another important feature of this invention is the flutter valve 36 appropriately supported by the flange member 35 from the bottom portion of the face mask 34, as best seen in FIG. 2. The purpose of this flutter valve or flapper valve is to permit easy exhaust of a welder's breath without the need for the exhaust to pass back through the filter element 40. Obviously if the exhaust were required to return by the same path as the filtered air entered, this would reduce the effectiveness of the over-all device, and also entail a slight buildup in exhaust pressure which would be undesirable.

Thus from the above description it can be seen how the protective welder's hood of this invention completely protects a user in many ways. He is protected visually by means of glass 16, he is protected physically by means of ear protectors 14 and neck protector 30, and his lungs and breathing system are protected by means of the air filter structure.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. In a protective hood for use by welders of the type including a headgear having a headband encircling the head above the ears and a top band connected to the headband and extending over the top surface of the head, a hood including a face panel and rearwardly extending side, top and bottom panels, means pivoting the free rear edge portions of the side panels to the headband forwardly of the ears to enable the hood to pivot to an inoperative position with the face panel above the top of the head, said face panel including window means therein alignable with the eyes to enable safe observation of the work area, the improvements comprising extensions on the rear edges of the side panels, said extensions extending substantially beyond the pivoting means and adapted to cover the ears of a welder when the hood is in operative position with the face panel in front of the face of the welder, a depending flexible flap attached to the rear edge of the bottom panel and disposed in front of the neck area of the welder when the hood is in operative position, a hollow, generally tubular face engaging mask disposed interiorly of the hood and including a rear peripheral end edge in sealing contact with the face of the welder in enclosing relation to the nose and mouth of the welder, the forward end edge of said mask being secured to said face panel in peripheral relation to an opening through said face panel, a one-way flutter type exhaust valve in said mask intermediate the end edges thereof to enable a welder to exhale therethrough, said opening in the face panel being defined by a forwardly extending flange having a peripheral inwardly extending abutment at the rear edge thereof, a filter element inserted into said flange and engaged with said abutment to filter inhaled air, and a removable annular cover engaged with said flange and overlying a portion of the peripheral forward surface of the filter element to removably secure the filter element in the opening to enable replacement thereof.

* * * * *